United States Patent [19]

Cohen et al.

[11] Patent Number: 5,102,786

[45] Date of Patent: Apr. 7, 1992

[54] BIOLOGICAL DIAGNOSTIC ASSAY SYSTEM

[75] Inventors: Saul G. Cohen; Shai Inbar, both of Boston, Mass.

[73] Assignee: PB Diagnostic Systems, Inc., Westwood, Mass.

[21] Appl. No.: 52,692

[22] Filed: May 21, 1987

[51] Int. Cl.⁵ ............................................. G01N 33/535
[52] U.S. Cl. ...................................... 435/7.9; 435/7.92; 435/7.93; 435/7.94; 435/962; 435/970; 436/518; 436/825; 422/56; 422/57
[58] Field of Search ................... 435/7, 805, 7.9, 7.92, 435/7.93, 7.94, 970, 962; 436/501, 140, 800, 810, 825, 805, 518; 422/56, 57

[56] References Cited

U.S. PATENT DOCUMENTS

| | | | |
|---|---|---|---|
| 3,911,096 | 10/1975 | Chopra | 424/1 |
| 3,928,553 | 12/1975 | Hollander | 424/1 |
| 4,468,469 | 8/1984 | Atkinson et al. | 436/826 |
| 4,622,293 | 11/1986 | Ellis et al. | 435/7 |
| 4,668,619 | 5/1987 | Greenquist et al. | 435/7 |

*Primary Examiner*—Esther M. Kepplinger
*Attorney, Agent, or Firm*—Gaetano D. Maccarone

[57] ABSTRACT

There is provided a biological diagnostic assay system wherein a phenoxy-substituted naphthalene compound, such as phenoxynaphthalene sulfonate, or a salt thereof, is utilized to prevent plasma proteins such as serum albumin from binding to other components of the assay and/or to displace plasma proteins which have become bound to other components of the assay.

31 Claims, No Drawings

BIOLOGICAL DIAGNOSTIC ASSAY SYSTEM

BACKGROUND OF THE INVENTION

The present invention relates to assays for the determination of biologically active components of biological fluids such as whole blood, plasma or serum.

Many assay elements for the rapid analysis of analytes present in biological fluids are known in the art. Of particular interest are those which are capable of performing the analysis with samples of whole blood since these avoid the need for prior separation of blood cells from plasma such as by centrifugation or extraction. There are known dry multilayer analytical elements to which the sample, e.g., a drop of whole blood, is applied and the cells (erythrocytes, leucocytes) are separated from the plasma by a filter element and the plasma, which includes the analyte of interest, then migrates to a reagent layer or layers. As a result of the interaction between the analyte and the reagent(s) present, a detectable change is brought about in the element corresponding to the presence of the analyte. The detectable change can be color change which may be evaluated visually or read spectrophotometrically such as with a densitometer. In another scheme based on the presence of fluorescent-labeled biologically active species, a fluorescent output signal can be generated and read spectrofluorometrically.

In order to obtain accurate and reproducible results with assay elements in general and particularly those wherein the sample used is whole blood or plasma, it is essential that the analytes of interest and the reagent(s) used be available to take part in the interaction(s) which bring about the detectable change. Unfortunately, however, dyes such as fluorescein, rhodamines, etc. and various biologically active compounds, particularly drugs which are "small molecules" having a molecular weight of up to 2000, for example, phenobarbital and phenytoin, and hormones such as thyroxine (T4) bind to plasma proteins. The affinity of these species to plasma proteins can of course adversely affect the accuracy of the results obtained, particularly when the sample is undiluted. Thus, where the compounds are present initially in the whole blood or plasma sample they will have complexed with the plasma proteins and must be displaced or dissociated to an analytically significant degree so that the resulting total free biologically active species can be determined. In the case of dyes, dye conjugates and other compounds which are used as reagents in the assay it is necessary to either prevent them from becoming bound to the plasma proteins, or if bound, displace or dissociate them.

Various compounds have been disclosed as being useful for this purpose in immuoassays. U.S. Pat. No. 3,911,096 refers to various materials as being useful as blocking agents for T4 including, for example, 8-anilino-1-naphthalene-sulfonic acid (ANS), naphthalene sulfonic acid, 2, 4, 6-trinitrobenzene sulfonic acid (TNBS) and others. U.S. Pat. No. 3,928,553 refers to various binding inhibitory agents for triiodothyronine and thyroxine such as barbituric acid and its derivatives, salicylates and sodium diethylmalonylurea. U.S. Pat. No. 4,622,293 teaches the use of 2-hydroxy-4-methoxybenzophenone-5-sulfonic acid (HMS) as a blocking agent in iodothyranine assays.

The known blocking agents are not satisfactory in all instances. These agents desirably should possess various properties in order to function effectively. For example, the blocking or displacing agent should not interfere with the specific binding pair interaction which is exploited to provide the detectable signal. Further, in assays which utilize a fluorescent-labeled analyte and a fluorescent output signal is generated, the blocking or displacing agent should not exhibit any substantial fluorescence itself, or when complexed to plasma proteins, in the same excitation and emission ranges as the fluorescent label. In addition they should not quench the fluorescence of the label. Accordingly, there is a continuing need for blocking or displacing agents which can be used in diagnostic assays without adversely affecting the accuracy of the analysis.

BRIEF SUMMARY OF THE INVENTION

The present invention provides a diagnostic assay system wherein phenoxy-substituted naphthalene compounds and salts thereof, are utilized as blocking and/or displacing agents. The phenoxy-substituted naphthalene compounds are represented by the formula

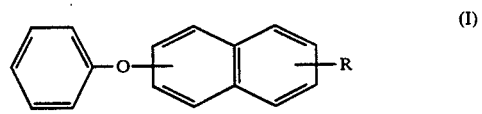

(I)

wherein R is an ionic group, such as a sulfonic acid, a carboxylic acid, a phosphonic acid or the like, which can be attached to any carbon atom on the naphthalene ring structure.

By an "ionic group" as used in the specification and claims herein, is meant a group which will ionize in water and thereby improve solubility of the molecule. Typical suitable ionic groups which may be incorporated in the compounds include sulfonic acid (—SO₃H), carboxylic acid (—COOH), phosphonic acid (—OP(OH)₂) and the like.

The salts of the compounds encompassed by Formula I are represented by the formula

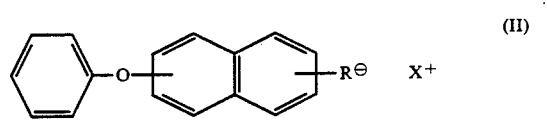

(II)

wherein X is any biologically acceptable cation such as Na⁺, K⁺ and the like.

As noted above, the substituent R may be appended to any carbon atom of the naphthalene ring structure. In a particularly preferred embodiment of the invention 1-phenoxynaphthalene-8-sulfonic acid (PNS) and its salts are utilized as blocking and/or displacing agents. PNS is represented by the formula

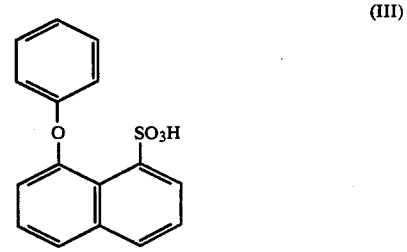

(III)

It has been found that PNS and its salts can be included in assays at concentrations effective to block the binding of assay components to plasma proteins and/or displace initially bound components, by an analytically significant amount, typically more than 50%, and preferably more than 75%, while not interfering in any significant way with the accuracy of the assay. PNS has been found to be effective to block the binding of plasma proteins to, or displace initially bound proteins from, components of the assays such as: dyes which are used as labels for analytes, for example, fluoresceins, rhodamines, etc.; conjugates of such dyes with biologically active species; drugs such as phenobarbital and phenytoin; and hormones such as thyroxine (T4). Further, at the concentrations required to perform these functions, PNS advantageously does not exhibit any substantial fluorescence in solution and does not quench to any significant extent the fluorescence of such dyes in solution. PNS, in hydroxyethyl piperazine ethyl sulfonate (HEPES) buffer (pH 7.2) exhibits an absorption maximum at 304 nm ($\epsilon = 3.5 \times 10^3$). In the same buffer, PNS exhibits an emission maximum at 414 nm (excitation at 290 nm) and fluoroscence quantum yield, (Qf)=0.54, in ethanol.

The amount of phenoxy-substituted naphthalene compounds and their salts required in any particular assay will vary and is dependent upon factors such as the particular analyte being determined, the amount of the analyte present in the sample, the other components which enter into the assay reactions, etc. Routine scoping tests can be used to determine the effective amount for any particular assay. Typically, from about 0.05% to about 2%, by weight, of the phenoxy-substituted naphthalene compound, based on the total weight of the reactants, will be required.

The phenoxy-substituted naphthalene compounds and their salts are soluble in water at the required concentrations at the pH at which the assays are carried out. For example, at very low pH, i.e., below pH 3, PNS will become protonated and precipitate from solution. Typically, the immunoassays are carried out at a pH above 3, preferably in the range of from 6 to 8. In the pH range of interest PNS is soluble in water at the required concentrations.

DESCRIPTION OF THE PREFERRED EMBODIMENTS

The present invention encompasses the use of phenoxy-substituted napthalene compounds and their salts in biological diagnostic assays generally. In a preferred embodiment there are provided immunoassays in which these compounds and their salts are utilized, that is, assays which are based on antigen-antibody interactions. The antigens include those which have a molecular weight of from about 100 to about 2000, more typically from about 125 to about 1000, for example, drugs such as alkaloids, steroids, benzheterocyclics, purines, etc. The antibodies may be polyclonal antibodies, monoclonal or fragments thereof. The assays may be conducted according to conventional "wet" techniques or they may be carried out with a "dry" assay element which may be a multilayer element. Such dry assay elements are known in the art and therefore extensive discussion of such assay elements is not required here. These assay elements may be made up of a single layer of a liquid permeable matrix material such as a membrane of substantially uniform porosity which has dispersed in at least a part thereof a diagnostic reagent composition. U.S. Pat. No. 3,607,093 discloses an assay element of this type. Alternatively, such assay elements are comprised of a plurality of layers with the various layers performing one or more functions. For example, U.S. Pat. No. 3,368,872 discloses a multilayer analytical element for the analysis of biological liquids which includes a porous tape for receiving the sample. This receiving layer is provided on the test layer. The sample, which may be a drop of blood, is applied to the porous receiving tape which functions to spread, or distribute, the sample evenly over the reagent layer. U.S. Pat. No. 3,723,064 also discloses a multilayer analytical device which includes a porous layer for receiving the sample. The porous material has uniform porosity which allows capillary migration to provide an even distribution of the components in the test fluid prior to entering the adjacent reagent layer. Thus, the multilayer elements according to the present invention preferably include a layer or other means which can receive a drop of test fluid and provide an even distribution of the components of the test fluid to a reagent layer. In another embodiment, the assay element may include a filter element to remove cells (erythrocytes, leucocytes, etc.) or other interfering species from the fluid.

The assay elements of the invention may include a plurality of reagent layers, each of which includes a reagent which takes part in the signal-generating system which is utilized in the element. There may also be included various other layers such as, for example, a layer adapted to receive a diffusible signal-generating species formed as a result of the reactions or interactions which occur or a fluid permeable, light-blocking layer appropriately arranged in the element to assist in detecting the signal generated in the elements. The phenoxy-substituted naphthalene compound may be incorporated in any appropriate layer of these analytical elements. In multilayer elements which include a filter element and/or a sample spreading, or distribution, layer the compound is preferably incorporated in the filter layer or the sample spreading layer.

The present invention encompasses any biological diagnostic assay method for the anaysis of a component in a biological fluid. Preferred methods are immunoassays based on antigen—antibody interactions including competitive assays and immunometric and sandwich assays of all types. Typically, these immunoassays involve a labeled reagent. Any chemical interaction which effects a change in the radiation emission in either the label of the labeled reagent or a reagent which interacts with the label to cause a change in radiation emission to provide a detectable signal can be exploited in such assays. For example, any change in fluorescence, chemiluminescence, color or other change in visible or near visible radiation can be exploited. Thus, the label utilized in such immunoassays can be directly or indirectly detectable. The label may be a fluorophore, chromophore, chemiluminophore, a phosphor or an enzyme. Where the label is an enzyme it can be one which interacts with a substrate to cause a change in absorption where the substrate is a chromogen, in fluorescence if the substrate is a fluorophor, in chemiluminescence where the substrate is a chemiluminescent precursor or in phosphorescence where the substrate is a phosphor.

The invention will now be described further in detail with respect to specific preferred embodiments by way of examples, it being understood that these are intended to be illustrative only and the invention is not limited to the materials, procedures, etc. which are recited therein.

EXAMPLE I

Displacement of Phenobarbital from Plasma Protein

Solutions of human plasma containing 0% (control), 0.02%, 0.05%, 0.2% and 0.5% respectively, of PNS were prepared and to each was added 0.1% of Tween 20 (Rohm and Haas) a surfactant. A 50 mmolar solution of radioactive tritium-labeled ethyl-5-phenyl-barbituric acid, 5—[$^3$H (G)] (New England Nuclear) in HEPES buffer was also prepared.

The phenobarbital solution (10 μl) was added to each of the PNS-plasma solutions and they were then incubated from 1 hour at room temperature. The solutions were then centrifuged at 5000 g through a Centricon PM 10 filter (Amicon Corp.) which passes only molecules having molecular weight below 10,000. Thus, any phenobarbital bound to proteins will not pass through the filter. The filtrates (25 μl) were each diluted with 10 ml of BIOFLUOR, a scintillation fluid and the radioactivity counted with a Scinti Verse ™ BIO-HP (Fisher Scientific). The results are shown in Table I.

TABLE I

| PNS CONC. (% in plasma) | % PHENOBARBITAL (±3%) (passed through filter) |
| --- | --- |
| 0 | 55.5 |
| 0.02 | 62.7 |
| 0.05 | 71.1 |
| 0.2 | 93.0 |
| 0.5 | 97.0 |

It can be seen that about 45% of the total phenobarbital was bound to plasma proteins and did not pass through the filter. The results show that the PNS was effective to dissociate phenobarbital from the plasma proteins with the optimum dissociation being obtained with 0.5% PNS.

EXAMPLE II

Displacement of Sulforhodamine 101 from Human Serum Albumin (HSA).

Two sets of aqueous solutions, 1.05×10$^{-5}$M in sulforhodamine 101, were prepared in HEPES buffer with varying amounts of HSA. One set (Control) did not contain any PNS and the other contained 0.2% PNS. The solutions were centrifuged through a Centricon 30 filter at 5000 g and the filtrates were scanned at 586 nm on a Perkin-Elmer λ9 spectrophotometer. The amounts of sulforhodamine 101 present in the filtrates are shown in Table II.

TABLE II

| | % SULFORHODAMINE 101 (PASSED THROUGH FILTER) | |
| --- | --- | --- |
| % HSA | CONTROL | 0.2% PNS |
| 0 | 100 | 100 |
| 0.032 | 83 | 99 |
| 0.064 | 50 | 94 |
| 0.13 | 32 | 88 |
| 0.16 | 23 | 83 |
| 0.32 | 10 | 68 |
| 0.48 | 6 | 61 |

It can be seen that the PNS was very effective in providing free sulforhodamine 101.

EXAMPLE III

Displacement of a Theophylline-Rhodamine Conjugate From Plasma Proteins.

This experiment was conducted with a conjugate represented by the formula

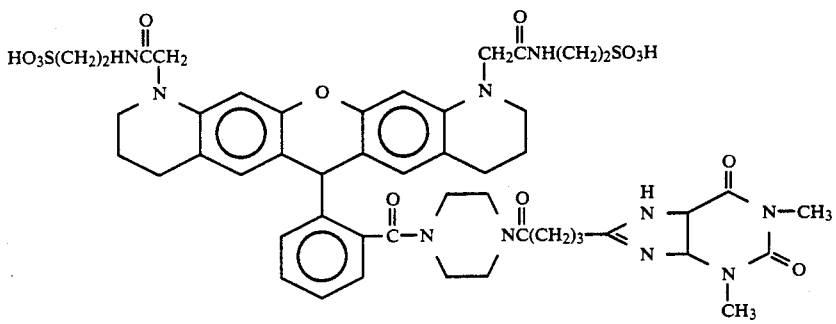

The conjugate is disclosed and claimed in commonly assigned, copending application Ser. No. 34,225, filed Apr. 2, 1987, now U.S. Pat. No. 4,900,686.

An experiment was carried out with the conjugate (1.0×10$^{-5}$M) dissolved in solutions of human plasma in HEPES buffer. One set of solutions (Control) did not contain any PNS and the other contained 0.2% PNS. The solutions were centrifuged through a Centricon 30 filter at 5000 g and the filtrates were scanned on a Perkin Elmer λ9 Spectrophotometer at 500–600 nm. The amounts of free conjugate in the filtrates are shown in Table III.

TABLE III

| | % CONJUGATE | |
| --- | --- | --- |
| % PLASMA | CONTROL | 0.2% PNS |
| 95 | 50 | — |
| 90 | — | 88 |
| 85 | 57 | — |
| 75 | — | 89 |
| 65 | 66 | — |
| 60 | — | 87 |
| 45 | 70 | — |
| 40 | — | 88 |
| 20 | 82 | 94 |
| 5 | 93 | — |
| 0 | 100 | 100 |

It can be seen that the PNS was very effective in providing free conjugate. Further, since plasma contains about 4% HSA it is apparent from the results obtained with the Control solutions that the conjugate became bound to other components in the plasma and the PNS was effective in blocking such binding and/or displacing bound conjugate.

EXAMPLE IV

Displacement of Fluorescein and a Fluorescein-Theophylline Conjugate from HSA.

Experiments were carried out with fluorescein and a fluorescein-theophylline conjugate, respectively, dissolved in HEPES buffer and containing various amounts of HSA. One set of solutions, (Control) did not contain any PNS and the other set contained 0.2% PNS. The solutions were centrifuged through a Centricon 30 filter at 5000 g and the filtrates were scanned at 490 nm. The results obtained are shown in Table IV.

TABLE IV

| | DYE | | CONJUGATE | |
|---|---|---|---|---|
| % HSA | CONTROL | 0.2% PNS | CONTROL | 0.2% PNS |
| 0 | 100 | 100 | 100 | 100 |
| 0.075 | 83 | 99 | 72 | 93 |
| 0.15 | 69 | 97 | 61 | 87 |
| 0.3 | 52 | 98 | 44 | 87 |
| 0.5 | 40 | — | 38 | — |
| 0.6 | 35 | 93 | 32 | 82 |
| 0.9 | — | 92 | — | 76 |
| 1.0 | 24 | — | 29 | — |
| 1.2 | 20 | 89 | 24 | 72 |
| 1.5 | 17 | 88 | 21 | 69 |

It can be seen that the PNS was effective in providing free dye and free conjugate.

EXAMPLE V

Displacement of Phenytoin from Plasma Proteins

Experiments were conducted with a set of plasma solutions in HEPES buffer containing $^{14}$C-labeled phenytoin ($9.3 \times 10^{-5}$M) and varying amounts of PNS. The solutions were filtered through a Centricon 30 at 5000 g and the filtrates were scintillation counted (100 μl of filtrate with 10 ml of scintillation fluid) using phenytoin in HEPES buffer as a reference. The results are shown in Table V.

TABLE V

| % PNS | % Phenytoin (±3) passed through filter |
|---|---|
| 0 | 11.9 |
| 0.1 | 97.5 |
| 0.2 | 98.6 |
| 0.3 | 98.7 |
| 0.4 | 98.6 |
| 0.5 | 96.7 |

It is apparent that the PNS was very effective in providing free phenytoin.

EXAMPLE VI

The fluorescent emissions of B- and R-phycoerythrin were studied as a function of PNS and 8-anilino-1-naphthalene sulfonic acid (ANS). The experiments were conducted with solutions of the phycoerythrin ($1.7 \times 10^{-10}$M) in HEPES buffer containing varying amounts of PNS and ANS. The phycoerythrins were excited at 560 nm and their emissions measured at 575 nm. The results are shown in Table VI.

TABLE VI

| % PNS or ANS | B-phycoerythrin rel. fl. intensity in the presence of | | R-phycoerythrin rel. fl. intensity in the presence of | |
|---|---|---|---|---|
| | PNS | ANS | PNS | ANS |
| 0 | 1.0 | 1.0 | 1.0 | 1.0 |
| 0.125 | 1.0 | 0.61 | 1.0 | 0.72 |
| 0.25 | 1.0 | 0.43 | 0.99 | 0.54 |
| 0.375 | 1.0 | 0.33 | 0.99 | 0.40 |
| 0.50 | 1.0 | 0.25 | 0.98 | 0.29 |

It can be seen that PNS does not affect the fluorescence emissions of the phycoerythrins in solution whereas ANS quenches the emissions of both phycoerythrins very strongly.

Although the invention has been described with respect to specific preferred embodiments, it is not intended to be limited thereto but rather those skilled in the art will recognize that variations and modifications may be made therein which are within the spirit of the invention and the scope of the appended claims. For example, other positions on the naphthalene ring structure can be appropriately substituted as can the positions on the phenyl ring of the phenoxy group. Thus, analogs possessing the advantageous blocking and/or displacing features of the phenoxy-substituted naphthalene compounds utilized according to the present invention will be considered as equivalents thereof for the purposes of the claims herein.

What is claimed is:

1. A method for determining a component in a biological fluid comprising contacting a biological fluid with at least a first reagent in the presence of a compound represented by the formula

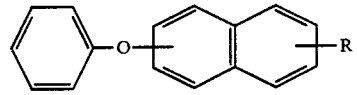

wherein
R is an ionic group and can be attached to any carbon atom on said naphthalene ring structure,
or a salt thereof, to produce a detectable change which is a function of a component in said biological fluid and detecting said change.

2. The method as defined in claim 1 wherein R is —SO$_3$H, —COOH or —OP(OH)$_2$.

3. The method as defined in claim 2 wherein said compound is represented by the formula

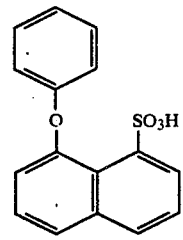

or a salt thereof.

4. The method as defined in claim 3 wherein said biological fluid is whole blood, plasma or serum.

5. The method as defined in claim 4 wherein said first reagent is a binding partner of said component to be determined.

6. The method as defined in claim 5 which is carried out in the presence of a second reagent.

7. The method as defined in claim 6 wherein said second reagent comprises a conjugate consisting of said component to be determined, or an analogue thereof, linked to a label.

8. The method as defined in claim 7 wherein said label is a fluorescent moiety.

9. The method as defined in claim 6 wherein said second reagent is a conjugate consisting of a binding partner of said component to be determined linked to a label.

10. The method as defined in claim 9 wherein said label is an enzyme and including reacting said enzyme with a substrate.

11. An immunoassay method for determining the presence of an analyte in a fluid sample comprising forming a binary complex of said analyte and its binding partner in the presence of a compound represented by the formula

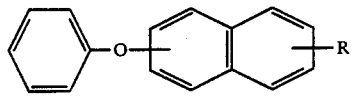

wherein
R is an ionic group and can be attached to any carbon atom on said naphthalene ring structure,
or a salt thereof, by contacting said sample with said binding partner.

12. The method as defined in claim 11 wherein R is —SO$_3$H, —COOH or —OP(OH)$_2$.

13. The method as defined in claim 12 wherein said compound is represented by the formula

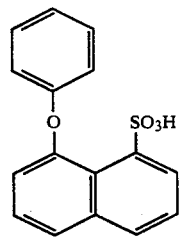

or a salt thereof.

14. The method as defined in claim 13 wherein said analyte is an antigen and wherein said step of contacting is carried out in the presence of a conjugate consisting of said antigen, or an analogue thereof, bound to a label.

15. The method as defined in claim 14 wherein said label is fluorescent.

16. An immunoassay method for determining the presence of an analyte in a fluid sample comprising forming a ternary complex of said analyte, a first binding partner and a second binding partner bound to said analyte at a different site than said first binding partner in the presence of a compound represented by the formula

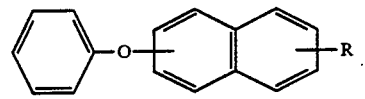

wherein
R is an ionic group and can be attached to any carbon atom on said naphthalene ring,
or a salt thereof, by contacting said sample with said first and second binding partners.

17. The method as defined in claim 16 wherein R is —SO$_3$H, —COOH or OP(OH)$_2$.

18. The method as defined in claim 17 wherein said compound is represented by the formula

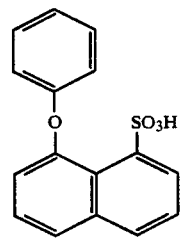

or a salt thereof.

19. The method as defined in claim 18 wherein said second binding partner is linked to a label.

20. The method as defined in claim 19 wherein said analyte is an antigen and said label is an enzyme.

21. An element for the analysis of a component in a biological fluid comprising at least one reagent layer and including a compound represented by the formula

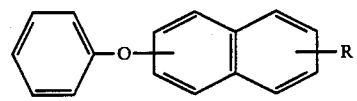

wherein
R is an ionic group and can be attached to any carbon atom on said naphthalene ring,
or a salt thereof.

22. The element as defined in claim 21 wherein R is —SO$_3$H, —COOH or —OP(OH)$_2$.

23. The element as defined in claim 22 wherein said compound is represented by the formula

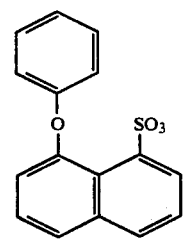

or a salt thereof.

24. The element as defined in claim 23 and further including a support.

25. The element as defined in claim 24 having two reagent layers and including a light-blocking layer arranged between said reagent layers.

26. The element as defined in claim 23 wherein said reagent layer includes a binding partner of the component in the biological fluid.

27. The element as defined in claim 26 and further including a conjugate consisting of the component to be analyzed for, or an analogue thereof, linked to a label.

28. The element as defined in claim 27 wherein said label is fluorescent.

29. The element as defined in claim 23 which includes a first binding partner for said component to be analyzed for and a second binding partner for said component to be analyzed for, each said binding partner adapted to bind to said component at a different site.

30. The element as defined in claim 29 wherein said second binding partner is linked to a label.

31. The element is defined in claim 30 wherein said label is an enzyme.

* * * * *